US00PP33690P2

(12) United States Plant Patent
van Sambeek

(10) Patent No.: US PP33,690 P2
(45) Date of Patent: Nov. 23, 2021

(54) ***COREOPSIS* PLANT NAMED 'DOCORMOSWIMP'**

(50) Latin Name: *Coreopsis grandiflora*
Varietal Denomination: Docormoswimp

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/139,899

(22) Filed: Dec. 31, 2020

(51) Int. Cl.
*A01H 6/14* (2018.01)
*A01H 5/02* (2018.01)

(52) U.S. Cl.
USPC ..... Plt./417

(58) Field of Classification Search
USPC ..... Plt./417
See application file for complete search history.

(56) References Cited

PUBLICATIONS

PLLUTO Plant Variety Database Apr. 17, 2021.*

* cited by examiner

*Primary Examiner* — Annette H Para
(74) *Attorney, Agent, or Firm* — C. Anne Whealy

(57) ABSTRACT

A new and distinct cultivar of *Coreopsis* plant named 'Docormoswimp', characterized by its upright and mounded plant habit; moderately vigorous growth habit and moderate growth rate; freely branching habit; medium green-colored leaves; freely flowering habit with numerous inflorescences per plant; double-type pompon inflorescences with yellow orange-colored ray florets; and good garden performance.

2 Drawing Sheets

Figure 1:
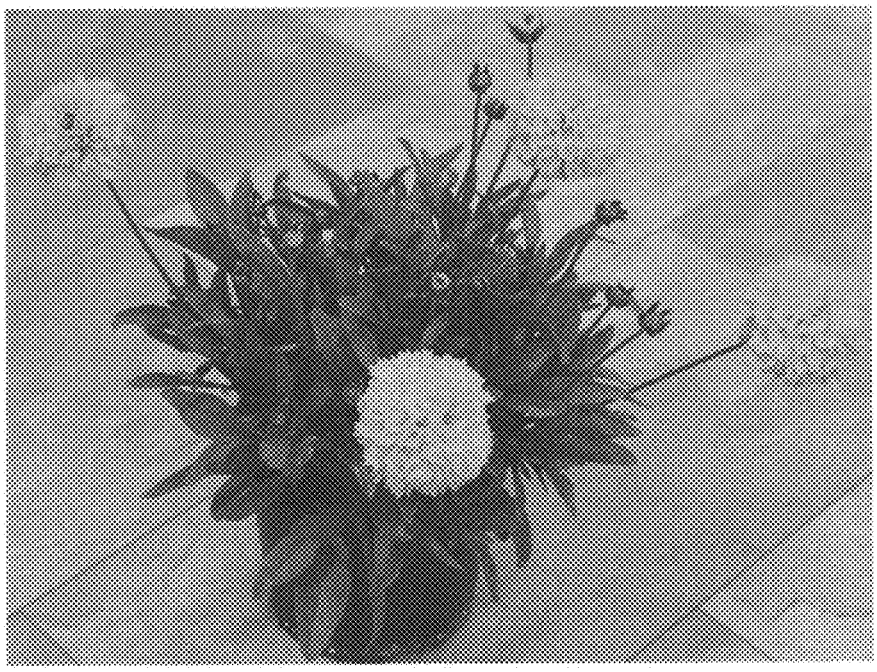

Botanical designation: *Coreopsis grandiflora.*
Cultivar denomination: 'DOCORMOSWIMP'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 24, 2020, application number 2020/1988. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Coreopsis* plant, botanically known as *Coreopsis grandiflora*, and hereinafter referred to by the name 'Docormoswimp'.

The new *Coreopsis* plant is a product of a planned breeding program conducted by the Inventor in Aalsmeer, The Netherlands. The objective of the breeding program is to create uniform *Coreopsis* plants with numerous double-type inflorescences.

The new *Coreopsis* plant originated from a cross-pollination made by the Inventor in Aalsmeer, The Netherlands in July, 2017 of a proprietary selection of *Coreopsis grandiflora* identified as code number CP13-000002-014, not patented, as the female, or seed, parent with a proprietary selection of *Coreopsis grandiflora* identified as code number CP13-000003-003, not patented, as the male, or seed, parent. The new *Coreopsis* plant was discovered and selected by the Inventor as a single flowering plant from within the progeny of the stated cross-pollination in a controlled environment in Aalsmeer in July, 2017.

Asexual reproduction of the new *Coreopsis* plant by vegetative cuttings in a controlled environment in Aalsmeer, The Netherlands since July, 2017 has shown that the unique features of this new *Coreopsis* plant are stable and reproduced true to type in successive generations.

SUMMARY OF THE INVENTION

Plants of the new *Coreopsis* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Docormoswimp'. These characteristics in combination distinguish 'Docormoswimp' as a new and distinct cultivar of *Coreopsis* plant:

1. Upright and mounded plant habit.
2. Moderately vigorous growth habit and moderate growth rate.
3. Freely branching habit.
4. Medium green-colored leaves.

5. Freely flowering habit with numerous inflorescences per plant.
6. Double-type pompon inflorescences with yellow orange-colored ray florets.
7. Good garden performance.

Plants of the new *Coreopsis* differ primarily from plants of the female parent selection in inflorescence form as inflorescences of plants of the new *Coreopsis* have more ray florets and are denser than inflorescences of plants of the female parent. In addition, disc florets of plants of the new *Coreopsis* are not conspicuous whereas disc florets of plants of the female parent are clearly visible.

Plants of the new *Coreopsis* differ primarily from plants of the male parent selection in inflorescence type as inflorescences of plants of the new *Coreopsis* are double pompon-types whereas inflorescences of plants of the male parent selection are semi-double types.

Plants of the new *Coreopsis* can be compared to *Coreopsis grandiflora* 'Decoreo16', disclosed in U.S. Plant Pat. No. 25,241. Plants of the new *Coreopsis* differ primarily from plants of 'Decoreo16' in peduncle length as plants of the new *Coreopsis* have longer peduncles than plants of 'Decoreo16'.

BRIEF DESCRIPTION OF THE PHOTOGRAPHS

The accompanying photographs illustrate the overall appearance of the new *Coreopsis* plant. The photographs show the colors as true as it is reasonably possible to obtain in colored reproductions of this type. Colors in the photographs may differ slightly from the color values cited in the detailed botanical description which accurately describe the colors of the new *Coreopsis* plant.

The photograph on the first sheet (FIG. 1) comprises a side perspective view of a typical flowering plant of 'Docormoswimp' grown in a container.

Figure 2:
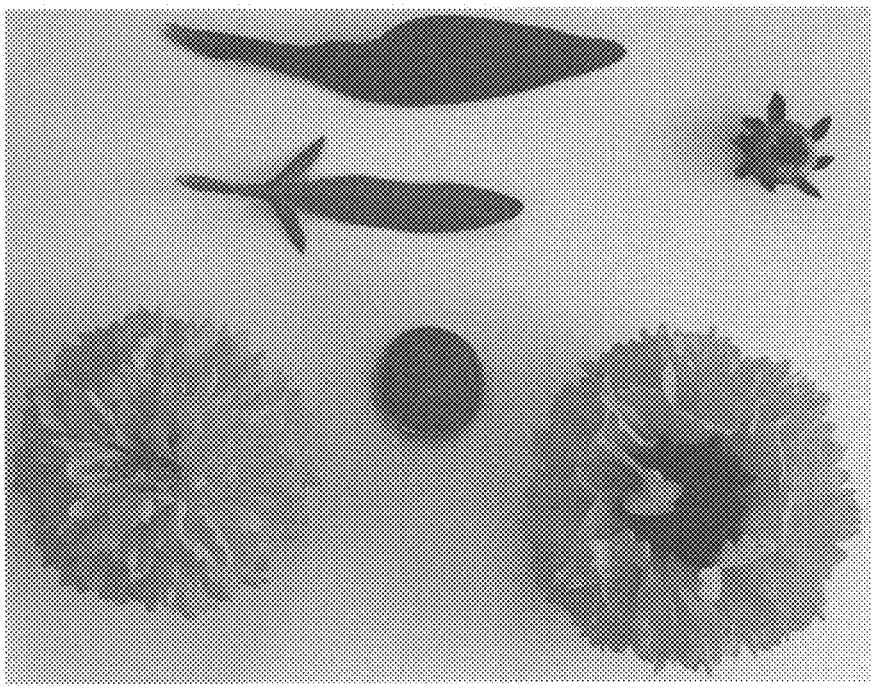

The photograph on the second sheet (FIG. 2) comprises close-up views of typical leaves (upper and lower surfaces), inflorescence bud and inflorescences (upper and lower surfaces) from a typical flowering plant of 'Docormoswimp'.

DETAILED BOTANICAL DESCRIPTION

The aforementioned photographs and following observations and measurements describe plants grown in 17-cm containers in Aalsmeer, The Netherlands during the summer initially in a greenhouse and finished in an outdoor nursery and under conditions and cultural practices which approximate those generally used in commercial *Coreopsis* plant production. During the production of the plants, day temperatures averaged 22° C. and night temperatures averaged 17° C. Plants were 17 weeks old when the photographs and description were taken. In the following description, color references are made to The Royal Horticultural Society Colour Chart, Second Edition, except where general terms of ordinary dictionary significance are used. Measurements represent averages for typical flowering plants.

Botanical classification: *Coreopsis grandiflora* 'Docormoswimp'.

Parentage:

*Female, or seed, parent.*—Proprietary selection of *Coreopsis grandiflora* identified as code number CP13-000002-014.

*Male, or pollen, parent.*—Proprietary selection of *Coreopsis grandiflora* identified as code number CP13-000003-003.

Propagation:

*Type.*—By vegetative cuttings.

*Time to initiate roots, summer.*—About 16 days at temperatures about 26° C.

*Time to initiate roots, winter.*—About three weeks at temperatures about 23° C.

*Time to produce a rooted young plant, summer.*—About 24 days at temperatures about 23° C.

*Time to produce a rooted young plant, winter.*—About four weeks at temperatures about 18° C.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright and mounding plant habit; broad inverted triangle; freely branching habit with about seven primary lateral branches each with about six secondary lateral branches; moderately vigorous growth habit and moderate growth rate.

*Plant height, soil level to top of foliar plane.*—About 19 cm.

*Plant height, soil level to top of floral plane.*—About 30 cm.

*Plant diameter or spread.*—About 36 cm.

*Lateral branches.*—Length: About 20 cm. Diameter: About 6 mm. Internode length: About 5 cm. Aspect: Upright to about 40° from vertical. Strength: Strong, flexible. Texture and luster: Pubescent; glossy. Color: Close to 144A.

Leaf description:

*Arrangement.*—Opposite, simple; sessile.

*Length.*—About 9.5 cm.

*Width.*—About 5.5 cm.

*Shape.*—Elliptic; lower leaves are entire and upper leaves are one or two-lobed.

*Apex.*—Acute.

*Base.*—Acuminate.

*Margin.*—Entire or deeply one to two-lobed; lobes are divergent; ciliate.

*Texture and luster, upper and lower surfaces.*—Pubescent; semi-glossy.

*Venation pattern.*—Pinnate.

*Color.*—Developing leaves, upper surface: Close to 137B. Developing leaves, lower surface: Close to 138B. Fully expanded leaves, upper surface: Close to 137B; venation, close to 137B. Fully expanded leaves, lower surface: Close to 138C; midvein, close to 141C and lateral venation, close to 138C.

Inflorescence description:

*Appearance.*—Double-type pompon terminal and axillary inflorescences with ray and disc florets arranged acropetally on a capitulum; inflorescences positioned above and beyond the foliar plane on strong peduncles; inflorescences face mostly upright.

*Flowering habit.*—Freely flowering habit; about 60 inflorescences developing per plant during the flowering season.

*Fragrance.*—Faintly fragrant; pleasant.

*Time to flower*.—Under natural season conditions, plants flower during June and July in The Netherlands; plants begin flowering about eight weeks after planting.

*Post-production longevity*.—Inflorescences maintain good substance for about three to four weeks on the plant; inflorescences persistent.

*Inflorescence buds*.—Height: About 1.2 cm. Diameter: About 1.4 cm. Shape: Rounded, flattened sphere. Texture and luster: Smooth, glabrous; glossy. Color: Close to 144A.

*Inflorescence size*.—Diameter: About 7 cm. Depth (height): About 4.5 cm. Disc diameter: About 6 mm. Receptacle height: About 6 mm. Receptacle diameter: About 2 cm. Receptacle color: Close to 152A.

*Ray florets*.—Quantity and arrangement: About 113 arranged in about eight whorls. Length: About 3.7 cm. Width: About 2 cm. Shape: Obovate. Apex: Emarginate; ragged appearance. Base: Acuminate. Margin: Entire; moderately undulate. Texture and luster, upper and lower surfaces: Smooth, glabrous; matte. Color: When opening, upper and lower surfaces: Close to 17A. Fully developed, upper and lower surfaces: Close to 17A; venation, close to 17A; color does not change with development.

*Disc florets*.—Quantity and arrangement: About 29 arranged in about four whorls; inconspicuous. Shape: Tubular, slender; apex dentate. Length: About 1.3 cm. Diameter: About 5 mm. Texture and luster: Smooth, glabrous; matte. Color, immature: Close to 17A. Color, mature: Close to 17A; color does not change with development.

*Phyllaries*.—Quantity and arrangement: About eight in a single whorl; fused at the base. Length: About 1.5 cm. Width: About 4 mm. Shape: Deltoid. Apex: Acuminate. Margin: Entire. Texture and luster, upper and lower surfaces: Smooth, glabrous; semi-glossy. Color, upper and lower surfaces: Close to 152A.

*Peduncles*.—Length: About 21 cm. Diameter: About 3 mm. Strength: Strong. Aspect: Mostly upright to outwardly. Texture and luster: Smooth, glabrous; glossy. Color: Close to 144A.

*Reproductive organs*.—Androecium (present on disc florets only): Quantity per disc floret: Five. Filament length: About 2 mm. Filament color: Close to 7A. Anther shape: Lanceolate. Anther size: About 3 mm by 0.5 mm. Anther color: Close to 166A. Pollen amount: Abundant. Pollen color: Close to 12A. Gynoecium (present on disc florets only): Quantity per floret: One. Pistil length: About 8 mm. Stigma diameter: About 2 mm. Stigma shape: Tri-parted. Stigma color: Close to 17A. Style length: About 7 mm. Style color: Close to 5A. Ovary color: Close to 145B.

*Seeds and fruits*.—To date, seed and fruit production has not been observed on plants of the new *Coreopsis*.

Pathogen & pest resistance: To date, plants of the new *Coreopsis* have not been shown to be resistant to pathogens and pests common to *Coreopsis* plants.

Garden performance: Plants of the new *Coreopsis* have exhibited good tolerance to rain, wind and to tolerate temperatures ranging from −30° C. to about 35° C. and to be suitable for USDA Hardiness Zone 4.

It is claimed:

1. A new and distinct *Coreopsis* plant named 'Docormoswimp' as illustrated and described.

* * * * *